Sept. 19, 1967 P. DICKSON Plant Pat. 2,769
ROSE PLANT
Filed Aug. 29, 1966
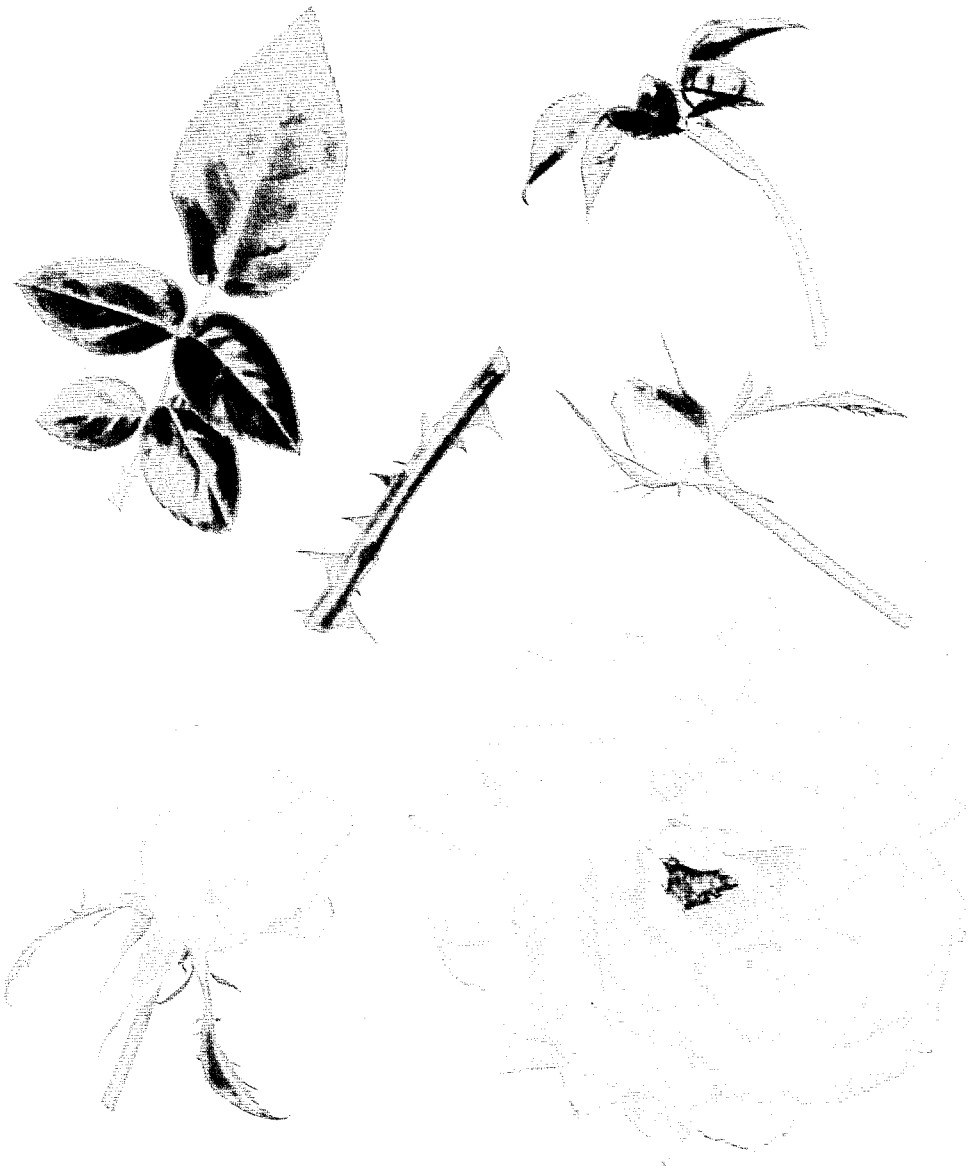
Inventor.
Patrick Dickson
By: Robb & Robb
Attorneys.

United States Patent Office

Plant Pat. 2,769
Patented Sept. 19, 1967

2,769
ROSE PLANT

Patrick Dickson, Newtownards, Ireland, assignor to Jackson & Perkins Company, Newark, N.Y., a corporation of New York

Filed Aug. 29, 1966, Ser. No. 575,910
1 Claim. (Cl. Plt.—11)

The present invention relates to a new and distinct variety of Rose plant of the hybrid tea class, which was originated by me by crossing an unnamed and unpatented seedling of "Governador Braga da Cruz" (unpatented) × "Kordes' Perfecta" (U.S. Plant Patent No. 1,604) with the variety known as "Piccadilly" (unpatented).

The primary objective of this breeding was to produce a new rose variety comparable to the variety known as "Peace" (U.S. Plant Patent No. 591), but which bears more colorful flowers. This objective was fully achieved along with other desirable improvements, as evidenced by the following unique combination of characteristics which are outstanding in the new variety and which distinguish it from its parents, as well as from all other varieties of which I am aware:

(1) A vigorous habit of plant growth attaining an average height of about 3½ feet;

(2) A large flower size;

(3) A high-centered flower form; and (4) A distinctive and attractive flower color corresponding to Maize Yellow, with the upper half of the flower petals being lightly overcast with Straw Yellow, and with the edge of the petals being overcast with Shell Pink.

Asexual reproduction of my new variety by budding, as performed at Newark, N.Y., U.S.A., and also at Pleasanton, Calif., U.S.A., shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
- *Seed parent.*—"Governador Braga da Cruz" × "Kordes' Perfecta."
- *Pollen parent.*—"Piccadilly."

Classification:
- *Botanic.*—Hybrid tea.
- *Commercial.*—Hybrid tea.

*Flower*

(Observations made from specimens grown outdoors at Newark, N.Y., U.S.A., in the early morning during the middle of the month of June.)

Blooming Habit: Recurrent—continuous.

Bud:
- *Size.*—Large.
- *Form.*—Ovoid; is not affected by wet or hot weather.
- *Color.*—When sepals first divide—Jasper Red, Plate 13. When petals begin to unfurl—Amber Yellow, Plate 16, lightly overcast with Nopal Red, Plate 1. When half-blown: inside of petals—Light Cadmium, Plate 4, edged slightly with Old Rose, Plate 13; reverse of petals—Empire Yellow, Plate 4 with upper half of petal overcast with Maize Yellow, Plate 4.
- *Sepals.*—Slightly branched; curl back when petals begin to unfurl. Color: inside—Rainette Green, Plate 31, with the lower half of sepal lightly overcast with Nopal Red, Plate 1; outside—Light Elm Green, Plate 17.
- *Calyx.*—Color—Light Elm Green, Plate 17. Shape—apple. Size—broad. Aspect—smooth. Odor when rubbed—none.
- *Peduncle.*—Length—long. Aspect—prickly. Strength—erect; heavy. Color—Kronberg's Green, Plate 31.
- *Opening.*—Opens up well; is not affected by adverse weather conditions.

Bloom:
- *Size.*—Large. Average size when fully expanded—5–5½ inches.
- *Borne.*—Both singly and several together.
- *Stems.*—Long; strong.
- *Form (when first open).*—High-centered. Permanence—retains its form to the end.
- *Petalage.*—Double (full but open center). Number of petals under normal conditions—from 35 to 40.
- *Color.*—Center of flower—Primuline Yellow, Plate 16. Outer petals—Straw Yellow, Plate 16 with edge of petal slightly overcast with Shell Pink, Plate 28. Base of petals (aiglet)—Barium Yellow, Plate 16. Inside of petals—Maize Yellow, Plate 4 with upper half of petal lightly overcast with Straw Yellow, Plate 16, and with edge of petal overcast with Shell Pink, Plate 28. Reverse of petals—Massicot Yellow, Plate 16. General tonality from a distance—Maize Yellow, Plate 4.
- *Discoloration.*—General tonality at end of first day—Maize Yellow, Plate 4. Second day—Maize Yellow, Plate 4. Third day—Maize Yellow, Plate 4, lightly overcast with Straw Yellow, Plate 16.

Petals:
- *Texture.*—Leathery; is not affected by wet or hot weather.
- *Appearance.*—Inside—satiny. Outside—shiny.
- *Form.*—Oval; slightly notched.
- *Arrangement.*—Imbricated (regularly arranged shingle-like).
- *Petaloids in center.*—Few; large.
- *Persistence.*—Drop off cleanly.
- *Fragrance.*—Moderate. Nature—tea (average hybrid tea scent).
- *Lasting quality.*—On plant—long. On cut flower—long.

*Genital organs*

Stamens, anthers: Medium size; many; regularly arranged around styles. Color—Ochraceous-Buff, Plate 15.

Stamens, filaments (threads): Medium length. Color—Cream-Buff, Plate 30.

Pollen: Color—Warm Buff, Plate 15.

Styles: Bunched; uneven length; medium length; thin.

Stigmas: Color—Carnelian Red, Plate 14.

Ovaries: All enclosed in calyx.

Hips: None.

Seeds: None.

*Plant*

Form: Bush.

Growth: Vigorous; upright; about 3½ feet tall.

Foliage: Compound of from 3 to 5 leaflets.
- *Size.*—Large.
- *Quantity.*—Abundant.
- *Color.*—New foliage: upper side—Yellowish Oil Green, Plate 5; under side—Lettuce Green, Plate 5, lightly overcast with Olive-Ocher, Plate 30 at the outer edge of the leaf. Old foliage: upper side —Cress Green, Plate 31; under side—Rainette Green, Plate 31.

*Shape.*—Oval pointed.

*Texture.*—Upper side—leathery. Under side—smooth.

*Ribs and veins.*—Prominent.

*Edge.*—Serrated (saw toothed).

*Serration.*—Both double and single; small.

*Leaf stem.*—Color—Lettuce Green, Plate 5. Under side—smooth.

*Stipules.*—Medium length; slightly serrated.

Wood:

*New wood.*—Color—Oil Yellow, Plate 5. Bark—smooth.

*Old wood.*—Color—Jade Green, Plate 31. Bark—smooth.

Thorns:

*Thorns.*—Quantity: on main stalks from base—many; on laterals from stalk—ordinary. Form—narrow base; medium length; some hooked downward and some hooked upward. Color (when young)—Glass Green, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous habit of plant growth attaining an average height of about 3½ feet, a large flower size, a high-centered flower form, and a distinctive and attractive flower color corresponding to Maize Yellow, with the upper half of the flower petals being lightly overcast with Straw Yellow, and with the edge of the petals being overcast with Shell Pink.

No references cited.

ABRAHAM G. STONE, *Primary Examiner.*

ROBERT E. BAGWILL, *Examiner.*